United States Patent
McIntyre

(10) Patent No.: US 6,610,018 B1
(45) Date of Patent: Aug. 26, 2003

(54) NON-INVASIVE DETERMINATION OF LEFT-VENTRICULAR PRESSURE

(76) Inventor: Kevin M. McIntyre, 160 Commonwealth Ave., Suite 801, Boston, MA (US) 02116

(*) Notice: Subject to any disclaimer, the term of this patent is extended or adjusted under 35 U.S.C. 154(b) by 0 days.

(21) Appl. No.: 10/077,179

(22) Filed: Feb. 14, 2002

(51) Int. Cl.[7] .................................... A61B 5/02
(52) U.S. Cl. .................................... 600/485
(58) Field of Search ............... 600/300, 301, 600/485–504, 508

(56) References Cited

U.S. PATENT DOCUMENTS

| | | | |
|---|---|---|---|
| 3,776,221 A | 12/1973 | McIntyre | 128/2.05 R |
| 4,203,451 A * | 5/1980 | Panico | 600/485 |
| 5,291,895 A | 3/1994 | McIntyre | 128/672 |
| 5,445,159 A * | 8/1995 | Cheng | 600/485 |
| 5,634,467 A | 6/1997 | Nevo | 128/672 |
| 5,882,311 A * | 3/1999 | O'Rourke | 600/485 |
| 6,511,436 B1 * | 1/2003 | Asmar | 600/500 |

* cited by examiner

Primary Examiner—Robert L. Nasser
Assistant Examiner—Patricia Mallari
(74) Attorney, Agent, or Firm—Fish & Richardson P.C.

(57) ABSTRACT

A left-ventricular pressure waveform is obtained non-invasively by obtaining pressure waveforms from first and second pressure measurements and selecting a segment from each of the first and second pressure waveforms. Each segment is associated with a different interval of a cardiac cycle. The segments are then time-shifted by an amount indicative of a relative time of occurrence of each of the first and second segments.

27 Claims, 3 Drawing Sheets

NON-INVASIVE DETERMINATION OF LEFT-VENTRICULAR PRESSURE

FIELD OF INVENTION

This invention relates to medical diagnostic devices, and in particular, to devices for measurement of pressure within the heart.

BACKGROUND

The pressure within the left ventricle of the heart is an important parameter in the treatment of heart disease. However, the measurement of that pressure is hampered by the need to insert a probe into the left ventricle. Such invasive measurements are costly, time-consuming, and potentially dangerous to the patient. As a result, despite its importance, the pressure within the left ventricle is only rarely measured directly.

There exist systems for non-invasively measuring left-ventricular pressure during limited portions of the cardiac cycle. For example, during the ejection phase, and in the absence of aortic valve disease, the left-ventricular pressure corresponds to the arterial pressure. During that portion of the cardiac cycle characterized by an open mitral valve, the left-ventricular pressure is (to the extent that the mitral valve is normal) virtually the same as the left-atrial pressure. This left-atrial pressure is in turn related to PCWP (pulmonary capillary wedge pressure), which can be measured non-invasively by using a device and methods described in McIntyre, U.S. Pat. No. 5,291,895, the contents of which are herein incorporated by reference.

SUMMARY

The invention provides software for extracting segments from the outputs of two or more non-invasive diagnostic devices, each of which provides data that is indicative of left-ventricular pressure over at least a portion of the cardiac cycle. As used herein, data indicative of left-ventricular pressure includes absolute and relative pressure data, as well as data showing a contour of a pressure waveform. The software of the invention then time-shifts the extracted segments to inscribe a continuous curve indicative of the left-ventricular pressure waveform.

In one practice of the invention, a left-ventricular pressure waveform is assembled by obtaining a first pressure waveform from a first non-invasive pressure measurement and a second pressure waveform from a second non-invasive pressure measurement. First and second segments are then selected from the first and second waveforms respectively. These segments are associated with first and second intervals of the cardiac cycle. The first and second segments are then time-shifted relative to each other by an amount indicative of a relative time of occurrence of each of the first and second segments.

As used herein, "pressure measurement" refers to the collection of data indicative of pressure, which, as defined earlier, means absolute and relative pressure data, as well as data showing or recording a contour of a pressure waveform.

The first pressure waveform can be a signal indicative of a left-atrial pressure or one indicative of arterial pressure. When the signal indicates left-atrial pressure, the method can include obtaining a shape of the waveform from an apex cardiogram and adjusting an amplitude of the waveform on the basis of a non-invasively measured diastolic pressure.

Selecting a first segment can include determining an occurrence of an event indicative of the first interval of the cardiac cycle. A suitable choice of event is activity of a heart valve, for example the mitral valve or the aortic valve. An easily detectable event is, for example, the transition of either the mitral valve or the aortic valve between an open state and a closed state. Such events can be identified by detecting an acoustic signature indicative of valve activity, by detecting an electrical signature indicative of valve activity, or by detecting a mechanical signature indicative of valve activity.

DETAILED DESCRIPTION

A system according to the invention synthesizes a left-ventricular pressure waveform over a complete cardiac cycle by piecing together segments of the left-ventricular pressure waveform, each of which provides the left-ventricular pressure waveform over a limited portion of the cardiac cycle. The constituent segments of the desired waveform, the data needed to shift those segments in time, and the data needed to calibrate the constituent segments are obtained from a collection of non-invasive diagnostic devises.

Figure 1:
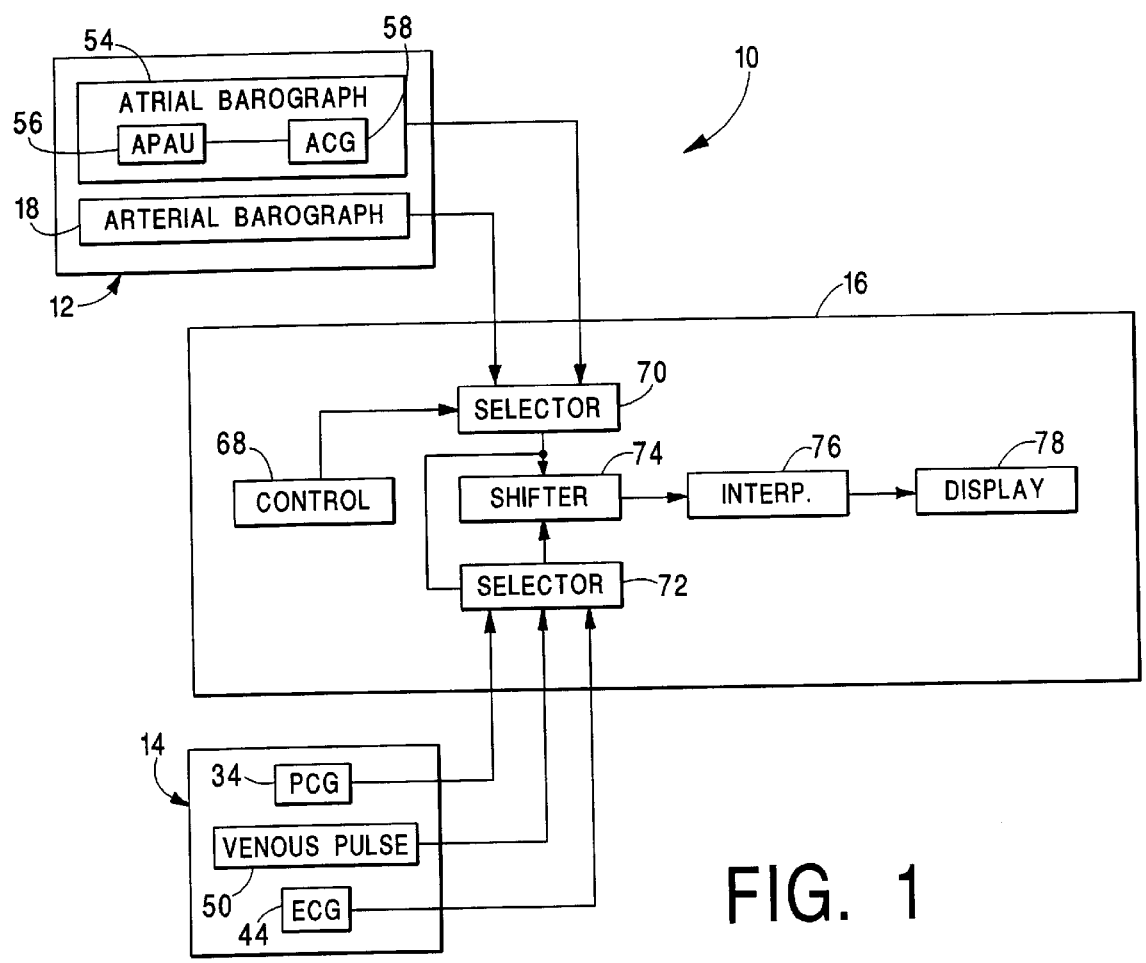
FIG. 1 shows a system for practice of the invention.

FIG. 1 shows a system 10 having two groups of diagnostic devices. A first group 12 includes non-invasive pressure measurement devices that provide signals indicative of a pressure waveform existing in a portion of the cardiovascular system. Such devices are collectively referred to herein as "barographs;" the pressure waveforms that they produce are collectively referred to as "barograms." A second group 14 includes non-invasive diagnostic devices that detect the occurrence of particular events during the cardiac cycle. These devices are collectively referred to as "event detectors." It will be appreciated that, in addition to providing data indicative of pressure, the output of one or more non-invasive pressure measurement devices from the first group 12 can also provide data indicative of the occurrence of particular events during the cardiac cycle.

The barograms and the outputs of the event detectors are provided to a software system 16 whose function is to select portions of the barograms and to synchronize those portions to form one continuous curve representative of the left-ventricular pressure during the entire cardiac cycle. This synthesized curve will be referred to herein as the "LV barogram".

One barograph from the first group 12 can be an arterial barograph 18 in non-invasive communication (i.e. by any non-invasive means) with a patient's arterial system. The arterial barograph 18 generates a waveform (shown in FIG. 2 and hereafter referred to as the "arterial barogram") that shows arterial pressure as a function of time. For that portion of the cardiac cycle during which the aortic valve is closed, the corresponding portion of the arterial barogram is not closely related to the left-ventricular pressure. However, during an ejection phase 28 of the cardiac cycle, the aortic valve is open and the left ventricle and aorta are (absent abnormalities of the aortic valve) in fluid communication with each other. Consequently, for those portions of the cardiac cycle, the arterial barogram does correspond to the LV barogram.

Figure 2:
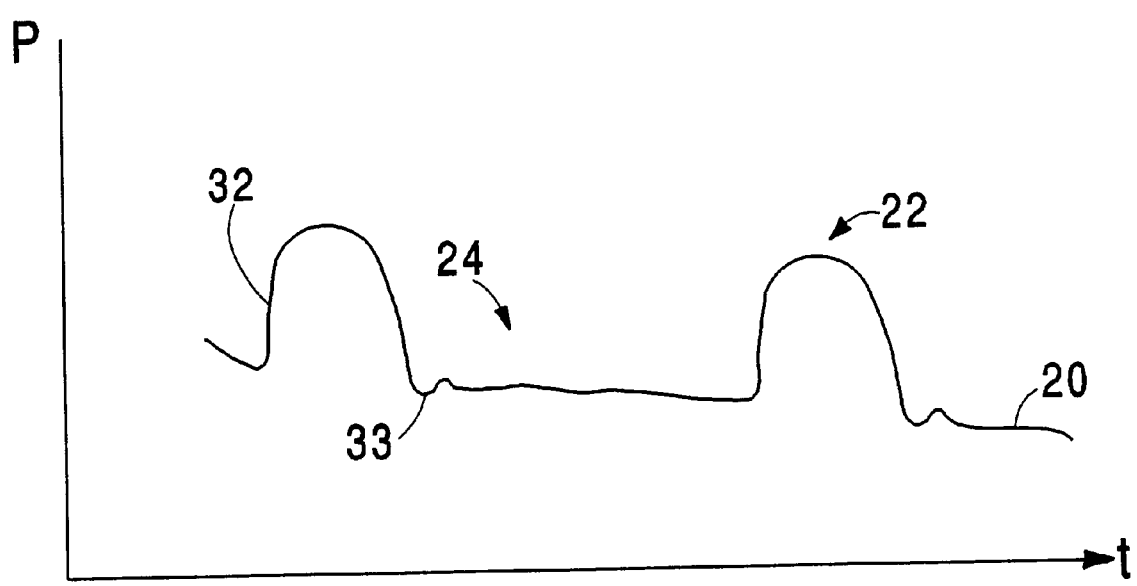
FIG. 2 shows an arterial barogram and an atrial barogram.

As shown in FIG. 2, an arterial barogram 20 thus includes a set of first portions 22 that are identical (absent abnormalities of the aortic valve) to the left-ventricular pressure, and a set of second portions 24 that are not relevant to the measurement of left-ventricular pressure. Each first portion 22 corresponds to a time interval during which the aortic valve is open. Each second portion 24 corresponds to a time interval during which the aortic valve is closed. To be of use in synthesizing the LV barogram, the arterial barogram 20 must therefore be further processed to discard the second portions 24 and to retain only the first portions 22. This requires the ascertainment of boundaries between the first and second portions 22, 24 of the arterial barogram 20.

Figure 3:
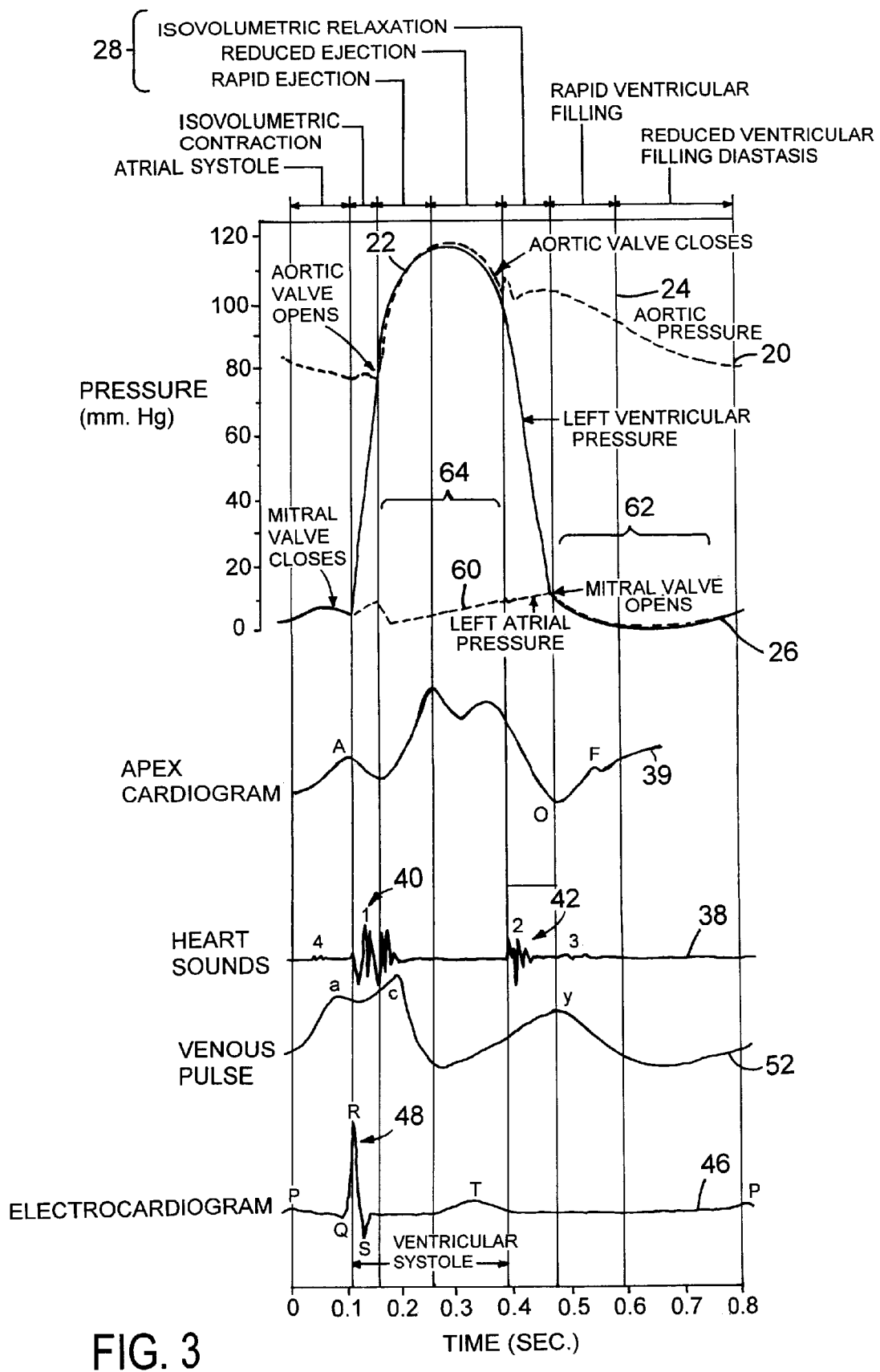
FIG. 3 shows LV pressure during a cardiac cycle.

FIG. 3 shows, for a patient in good cardiovascular health, a typical arterial barogram 20 overlaid on an LV barogram 26 obtained by direct measurement with a catheter in the left ventricle. A typical first portion 22 overlaps the LV barogram 26 during the ejection phase 28 of the cardiac cycle. A typical second portion 24 deviates significantly from the LV barogram 26. A time interval associated with the first portion 22 of an arterial barogram 20 will be referred to as a "pump interval" because during this interval, the left ventricle is pumping blood into the arterial system.

The opening and closing of the aortic valve delineate the extent of the pump interval. For the particular example shown in FIG. 2, the opening and closing of the aortic valve are associated with a sharp rise 32 in pressure and the occurrence of a dicrotic notch 33 respectively. However, in a patient with poor cardiovascular health, these features may not be as readily apparent. Even in cases where these features are apparent, the instants at which the aortic valve opens and closes cannot easily be determined with precision because the elasticity of the arteries, and other mechanical properties of the arterial system, can introduce delays in the response of the arterial pressure to the activity of the aortic valve. To some extent, these delays can be corrected for by correlating them with the occurrence of particular features in an electrocardiogram or phonocardiogram.

Certain events, such as the closing and opening of heart valves, are detected by one or more event detectors from the second group 14 of diagnostic devices shown in FIG. 1. These event detectors determine the instants at which certain key events in the cardiac cycle occur. These instants can then be used to identify boundaries between first and second portions 22, 24 of the arterial barogram 20.

For example, in the illustrated system 10, an event detector that includes a phonocardiograph 34 detects the acoustic signal generated by the aortic and mitral valves as they close. FIG. 3 shows, on the same time axis as the LV barogram 26, a representative phonocardiogram 38 provided by the phonocardiograph 34. As is apparent from FIG. 3, the beginning of a first acoustic pulse 40 marks the closing of the mitral valve. The beginning of a second acoustic pulse 42 marks the closing of the aortic valve. For event detectors that include a venous pulse acquisition unit 50, the "V" wave of the venous pulse 52 in FIG. 3 marks the opening of the mitral valve.

In some embodiments, an atrial barograph 54 can be used to identify the occurrence of particular events in the cardiac cycle. For those embodiments in which the atrial barograph 54 includes an apex cardiograph 58, certain features of the apex cardiogram can be used to identify the occurrence of events in the cardiac cycle. For example, the "O" point, or nadir of the apex cardiogram can be used to mark the opening of the mitral valve. FIG. 3 shows, on the same time axis as the LV barogram 26, a representative apex cardiogram 39 provided by the apex cardiograph 58.

Alternatively, an event detector can include an electrocardiograph 44. In such a case, the event detector uses selected features of an electrocardiogram to identify the occurrence of selected events. FIG. 3 shows an electrocardiogram 46 on the same time axis as the LV barogram 26. As is apparent from FIG. 3, the "R" spike of the QRS-wave 48 is associated with closing of the mitral valve. The opening of the aortic valve is known to occur after a known interval following the closing of the mitral valve and is also marked by the up-stroke of the aortic pressure trace.

As suggested above, an event detector can also include a venous pulse acquisition unit 50, a representative output of which is shown in FIG. 3 on the same time axis as the LV barogram 26. The output 52 of the venous pulse acquisition unit 50 has a peak associated with the opening of the mitral valve. Since the opening of the mitral valve may not be readily discernible in the phonocardiogram 38, the availability of data from the venous pulse acquisition unit 50 can be useful in fixing the time at which the mitral valve opens.

Following closure of the aortic valve, and the end of the pump interval, the left ventricle continues to relax. At some point, marked by the nadir of the apex cardiogram (indicated by "O" in FIG. 3), the pressure within the left ventricle falls to the point at which the mitral valve opens. This begins a fill interval, during which the mitral valve is open, the aortic valve is closed, and oxygenated blood flows into the left ventricle. In the absence of mitral valve disease, the left atrium and the left ventricle are in fluid communication during the fill interval. Hence, the left-ventricular pressure is a function of, or correlated with, the left-atrial pressure. Accordingly, a non-invasive measure of left-atrial pressure during the fill interval can provide information indicative of the atrial barogram.

Referring again to FIG. 1, in one embodiment, the first group 12 of diagnostic devices also includes an atrial barograph 54 in non-invasive communication with the patient's left atrium. The atrial barograph 54 provides a left-atrial pressure waveform, hereafter referred to as the "atrial barogram," that shows the left-atrial pressure as a function of time. The atrial barograph 54 thus provides an indication of ventricular pressure during the fill interval.

One example of an atrial barograph 54 includes an atrial-pressure acquisition-unit 56, such as that described in McIntyre U.S. Pat. No. 5,291,895, used in conjunction with an apex cardiograph 58. An atrial-pressure acquisition-unit 56 of the type disclosed therein provides values of atrial pressure at key points of the cardiac cycle. In particular, the atrial-pressure acquisition-unit 56 provides the LV pre-A EDP (pre-atrial contraction end diastolic pressure) and the LV post-A EDP (post-atrial contraction end diastolic pressure). The apex cardiograph 58 provides an apex cardiogram having the relative shape of the atrial pressure waveform. The absolute values of pressure from the atrial-pressure acquisition-unit 56 can thus be used to calibrate the apex cardiogram. The apex cardiogram and the pressure values provided by the atrial-pressure acquisition-unit 56 can thus be combined to provide the data needed to inscribe an atrial barogram.

Like the arterial barogram 20, the atrial barogram includes a set of first portions that are useful for the measurement of left-ventricular pressure and a set of second portions that are not relevant to the measurement of left-ventricular pressure. Each first portion corresponds to a fill interval during which the mitral valve is open. Each second portion corresponds to a pump interval during which the mitral valve is closed. Like the arterial barogram 20, the atrial barogram must be further processed to separate the first portions from the second portions. As was the case with the arterial barogram 20, this requires ascertainment of the boundaries between first and second sections.

FIG. 3 also shows a representative atrial barogram 60 superimposed on the same time axis as an LV barogram 26 measured directly by a catheter in the left ventricle. As is apparent from FIG. 3, the atrial barogram 60 tracks the LV barogram 26 closely during the fill interval, but deviates significantly once the mitral valve is closed.

In general, it may not be possible to reliably determine whether the mitral valve is closed by examining features of the atrial barogram 60. Moreover, since disease is detected by an improper response (pressure) to a stimulus (valve activity), it would be illogical to use the response to identify the occurrence of the stimulus. However, the same event detectors that were used to separate first and second portions of the arterial barogram 20 can be used to separate first and second portions of the atrial barogram 60.

As discussed above in connection with FIG. 3, the opening of the mitral valve can (in the absence of mitral valve disease) be detected on the basis of the nadir, or "O" point of the apex cardiogram or on the basis of the venous pulse 52. Closure of the mitral valve is associated with both the "R" spike on an electrocardiogram and with an acoustic pulse on the phonocardiogram 38.

The cardiac cycle also includes two, relatively brief intervals during which both the aortic valve and the mitral valve are closed. These intervals are referred to as the upstroke and downstroke intervals. The upstroke interval begins when, as the left ventricle begins its contraction, the left-ventricular pressure exceeds the left-atrial pressure. This causes the mitral valve to close. The upstroke interval ends when, as the left ventricle continues to contract, the pressure developed within the left ventricle exceeds the pressure in the aorta. This change in the sign of the pressure difference opens the aortic valve, thereby ending the upstroke interval and beginning the pump interval. The downstroke interval begins when, as the left ventricle relaxes, pressure in the aorta exceeds the declining left-ventricular pressure. The downstroke interval continues until the left ventricle relaxes enough to cause the left-ventricular pressure to fall below the left-atrial pressure. This change in the sign of the pressure difference opens the mitral valve, thereby ending the downstroke interval and beginning the fill interval.

During the upstroke and downstroke intervals, the fluid in the left-ventricle is isolated from the remainder of the circulatory system. Hence, it is not currently possible to obtain the shape of the pressure waveform during these relatively brief intervals. However, the upstroke and downstroke intervals are so brief that for all practical purposes, the LV barogram 26 during these intervals can be inscribed by connecting the known pressures at the beginning and end of the interval by a straight line.

In some cases, the derivative of the pressure waveform, particularly during the upstroke interval, is a useful quantitative indicator of heart function. Under these circumstances, one can empirically correct the pressure waveform during these intervals. Such correction factors may be required because the closure of the aortic valve is detected by measuring a pressure wave at a point far from the heart. As a result, there is a time delay between the closure of the aortic valve and the detection of that closure. This delay causes the measured derivative of the pressure waveform during the upstroke interval to be smaller than it should be. Such correction factors can be empirically determined by comparing LV measurements made directly and indirectly in a large number of patients and using statistics derived from such measurements to correct the measured derivative of the pressure waveform.

In other cases, the arterial barogram 20 can also provide information about additional hemodynamic parameters, such as stroke output and work performed by each stroke. This can be achieved by observing the duration of the pump interval and correlating that duration with stroke volume. A formula relating the duration of the pump interval with the stroke volume is well-known in the medical literature.

The area under the first portion 22 of the arterial barogram 20 can also provide information about these additional hemodynamic parameters. This can be achieved by obtaining calibration data using a non-invasive flow measurement technique. Such non-invasive flow measurement techniques include echo cardiography (as described on page 9 of vol. 6, No. 2 of a journal entitled "Congestive Heart Failure" and published in March/April 2000) Doppler measurements (as described in an article by Williams and Labovitz entitled "Doppler Estimation of Cardiac Output: Principles and Pitfalls" and published in Echocardiography 1987, pages 355–374) and non-invasive impedance determination of cardiac output (as described by Hanley and Stamer in "Pressure volume studies in man: an evaliation of the duration of the phases of systole" as published in 1969 in the Journal of Clinical Investigation, vol. 48, pp. 895–905. The calibration data thus obtained is thereafter used to determine the stroke volume from the integral of the arterial barogram 20 over the first portion. Because the characteristics of a patient's arterial system are relatively constant over time, any changes in the value of that integral will indicate a change in stroke output.

The software system 16 includes a first selection process 70 having inputs connected to barographs in the first group of diagnostic devices. The first selection process 70 has an output that corresponds to the LV barogram 26 during either the fill interval or the pump interval. The particular input to be selected is controlled by a control process 68 on the basis of what portion of the barogram was last inscribed.

Similarly, the software system also includes a second selection process 72 having inputs connected to event detectors in the second group of diagnostic devices. The second selection process 72, like the first, has an output that corresponds to a selected one of its inputs. The particular input to be selected depends on the output of the first selection process 70.

The software system 16 further includes a shift process 74 having a first and second input. The first input of the shift process 74 is connected to the output of the first selection process 70 and the second input of the shift process 74 is connected to the output of the second selection process 72. The output of the shift process 74 is its first input shifted in time by an amount derived from its second input.

The output of the shift process 74 is provided to an interpolation process 76 whose function is to inscribe the upstroke and downstroke intervals on the basis of the temporal endpoints of the pump and fill intervals and the values of the inscribed LV barogram 26 at those endpoints. The interpolation process 76 then provides its output to a display 78, which renders the LV barogram on a CRT, a strip chart, or any similar display.

Having described the invention, and a preferred embodiment thereof, what I claim as new and secured by Letters Patent is:

1. A method for non-invasively constructing a left-ventricular pressure waveform, the method comprising:

obtaining a first pressure waveform from a first non-invasive pressure measurement;

obtaining a second pressure waveform from a second non-invasive pressure measurement;

selecting a first segment from said first pressure waveform, said first segment being associated with a first interval of a cardiac cycle;

selecting a second segment from said second waveform, said second segment being associated with a second interval of said cardiac cycle; and time-shifting said first and second segments relative to each other by an amount indicative of a relative time of occurrence of each of said first and second segments.

2. The method of claim 1, wherein obtaining a first pressure waveform comprises obtaining a signal indicative of a left-atrial pressure.

3. The method of claim 2 wherein obtaining a signal indicative of a left-atrial pressure waveform comprises obtaining a shape of said signal from an apex cardiogram and adjusting an amplitude of said signal on the basis of an early diastolic pressure.

4. The method of claim 1, wherein obtaining a second pressure waveform comprises obtaining a signal indicative of an arterial pressure.

5. The method of claim 1, wherein selecting a first segment comprises determining an occurrence of an event indicative of said first interval of said cardiac cycle.

6. The method of claim 5, wherein determining an occurrence of an event comprises detecting a signal indicative of activity of a heart valve.

7. The method of claim 6, further comprising selecting said heart valve from the group consisting of a mitral valve and an aortic valve.

8. The method of claim 6 wherein detecting a signal indicative of activity of a heart valve comprises detecting a signal indicative of a transition between an open state of said heart valve and a closed state of said heart valve.

9. The method of claim 6, wherein detecting a signal indicative of activity of a heart valve comprises detecting an acoustic signature indicative of valve activity.

10. The method of claim 6, wherein detecting a signal indicative of activity of a heart valve comprises detecting signature indicative of valve activity, said signature being selected from the group consisting of an electrical signature and a mechanical signature.

11. The method of claim 1, wherein time-shifting said first and second segments relative to each other comprises connecting an end point of said first segment to a start point of said second segment.

12. The method of claim 11, wherein connecting an end point to a start point comprises defining a line connecting said end point and said start point.

13. A system for non-invasively constructing a left-ventricular pressure waveform, said system comprising:

a first amplitude sensor for non-invasively obtaining a first pressure waveform;

a second amplitude sensor for non-invasively obtaining a second pressure waveform;

an event sensor for detecting a time of occurrence of an event in a cardiac cycle; and a processor in communication with said first and second amplitude sensors and with said event sensor, said processor being configured to select a segment from each of said first and second waveforms and to connect said segments on the basis of said time of occurrence of said event.

14. The system of claim 13 wherein said first amplitude sensor comprises an atrial pressure sensor.

15. The system of claim 14, wherein said atrial pressure sensor comprises an apex cardiograph in communication with an atrial-pressure acquisition-unit.

16. The system of claim 13 wherein said second amplitude sensor comprises an arterial pressure sensor.

17. The system of claim 13 wherein said event detector is selected from the group consisting of an electrocardiograph and a phonocardiograph.

18. A method of non-invasively obtaining a left-ventricular pressure waveform, said method comprising:

selecting, from a first signal, a first signal portion that corresponds to a first phase of a cardiac cycle;

selecting, from a second signal, a second signal portion that corresponds to a second phase of said cardiac cycle;

determining a temporal relationship between said first and second signal portions; and time-shifting said first and second signal portions consistent with said temporal relationship.

19. A system for non-invasively generating a ventricular pressure waveform, said system comprising:

a non-invasive barograph for obtaining first data and second data indicative of first and second pressures within a ventricle, said first and second pressures being temporally separated from each other;

a non-invasive event detector for obtaining third data indicative of an occurrence of an event in the cardiac cycle; and a data processor configured to receive said first, second and third data and to combine said first and second data on the basis of said third data to construct therefrom, a ventricular pressure waveform.

20. The system of claim 19, wherein said data processor comprises a shifting process, said shifting process configured to temporally shift said first data on the basis of said second data.

21. The system of claim 20, wherein said data processor further comprises a calibration process, said calibration process configured to assign corresponding pressures to said first and second data.

22. The system of claim 19, wherein said non-invasive barograph comprises an atrial barograph.

23. The system of claim 22, wherein said atrial barograph comprises an apex cardiograph.

24. The system of claim 19, wherein said non-invasive barograph comprises an arterial barograph.

25. The system of claim 19 wherein said non-invasive event detector is selected from the group consisting of a phonocardiogram, a venous pulse acquisition unit, and an apex cardiograph.

26. The system of claim 19, wherein said non-invasive event detector comprises a venous pulse acquisition unit.

27. The system of claim 19, wherein said non-invasive event detector comprises an apex cardiogram.

* * * * *